United States Patent [19]

Robertson et al.

[11] Patent Number: 5,238,959
[45] Date of Patent: Aug. 24, 1993

[54] 3-PHENYLOXY-3-PHENYL PROPANAMINES

[75] Inventors: David W. Robertson, Greenwood; David T. Wong, Indianapolis, both of Ind.

[73] Assignee: Eli Lilly and Company, Indianapolis, Ind.

[21] Appl. No.: 871,616

[22] Filed: Apr. 20, 1992

Related U.S. Application Data

[63] Continuation of Ser. No. 617,467, Nov. 20, 1990, abandoned, which is a continuation of Ser. No. 179,368, Apr. 8, 1988, abandoned.

[51] Int. Cl.$^5$ .................... C07C 93/08; A61K 31/135; A61K 31/085
[52] U.S. Cl. ..................... 514/604; 514/620; 514/651; 564/346; 564/357; 564/353; 564/354
[58] Field of Search ............... 564/302, 346, 347, 353, 564/354, 355; 514/604, 607, 620, 651

[56] References Cited

U.S. PATENT DOCUMENTS

| | | | |
|---|---|---|---|
| 3,309,404 | 3/1967 | Engelhardt | 260/556 |
| 3,324,170 | 6/1967 | Kollonitsch | 260/471 |
| 3,922,305 | 11/1975 | Engelhardt | 260/570.8 TC |
| 4,018,895 | 4/1977 | Molloy et al. | 424/330 |
| 4,194,009 | 3/1980 | Molloy et al. | 424/330 |
| 4,243,681 | 1/1981 | Morrow et al. | 424/330 |
| 4,314,081 | 2/1982 | Molloy et al. | 564/347 |
| 4,500,541 | 2/1985 | Hausberg et al. | 514/466 |
| 4,584,404 | 4/1986 | Molloy et al. | 564/347 |
| 4,626,549 | 12/1986 | Molloy et al. | 514/651 |
| 4,692,469 | 9/1987 | Watthey | 514/651 |

FOREIGN PATENT DOCUMENTS

| | | |
|---|---|---|
| 0178874 | 4/1986 | European Pat. Off. . |
| 2026487 | 2/1980 | United Kingdom . |
| 1585036 | 2/1981 | United Kingdom . |

OTHER PUBLICATIONS

Wolff; in "Burger's Medicinal Chemistry"; Part III; 4th Ed.; p. 1043: 1979.

Primary Examiner—Marianne M. Cintins
Assistant Examiner—Michael B. Hydorn
Attorney, Agent, or Firm—Robert A. Conrad; Leroy Whitaker; Nancy J. Harrison

[57] ABSTRACT

The present invention provides 3-(4-substitutedphenoxy)-3-phenyl propanamines capable of inhibiting the uptake of serotonin. These compounds are useful for treating many pharmacological disorders, including depression and obesity. These compounds can also be used to reduce the desire to smoke and consume alcohol.

23 Claims, No Drawings

3-PHENYLOXY-3-PHENYL PROPANAMINES

This application is a continuation of application Ser. No. 07/617,467, filed on Nov. 20, 1990, now abandoned; which in turn is a continuation of application Ser. No. 07/179,368, filed on Apr. 8, 1988, now abandoned.

BACKGROUND OF THE INVENTION

During the past decade, the relationship between monoamine uptake and a variety of diseases and conditions has been appreciated and investigated. For example, the hydrochloride salt of fluoxetine (dl-N-methyl-γ-[4-(trifluoromethyl)phenoxy]benzenepropanamine) is a selective serotonin (5-hydroxytryptamine) uptake inhibitor presently undergoing clinical evaluation for the treatment of depression, anxiety, appetite suppression, and other disorders. Similarly, tomoxetine hydrochloride ((−)-N-methyl-γ-(2-methylphenoxy)benzenepropanamine hydrochloride) is a selective inhibitor of norepinephrine uptake being investigated clinically for its antidepressant activity. These compounds are among many taught in U.S. Pat. Nos. 4,018,895, 4,194,009, and 4,314,081 as being potent but selective blockers of the uptake of a particular monoamine.

SUMMARY OF THE INVENTION

The present invention provides novel 3-phenyloxy-3-phenyl propanamines which are selective and potent inhibitors of serotonin uptake. More specifically, the present invention relates to compounds of the Formula I

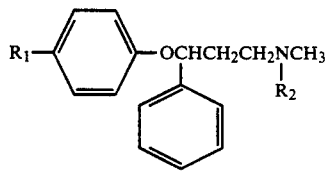

I wherein:
  $R_1$ is $(C_1-C_2\ alkyl)-S(O)_p-$, $CF_3S-$, $CF_3O-$, $H_2NCO-$, $H_2NSO_2-$, or $CH_3SO_2NH-$;
  $R_2$ is hydrogen or methyl;
  p is 0, 1, or 2; and
  the pharmaceutically acceptable acid addition salts thereof.

The invention also provides pharmaceutical formulations comprising a compound of the above formula and a pharmaceutically acceptable carrier, diluent or excipient therefor.

Further embodiments of the invention are methods for selectively inhibiting the uptake of serotonin, as well as for treating a variety of disorders which have been linked to decreased neurotransmission of serotonin in mammals including obesity, depression, alcoholism, pain, loss of memory, anxiety, smoking, and the like, employing a compound of the invention.

DETAILED DESCRIPTION OF THE INVENTION

Preferred compounds are those wherein $R_2$ is hydrogen. Also preferred are compounds wherein $R_1$ is $CH_3S-$. The most preferred compound of this series is N-methyl-γ-[4-(methylthio)phenoxy]benzenepropanamine and pharmaceutically acceptable acid addition sa thereof. The term "($C_1-C_2$ alkyl)" refers to methyl and ethyl.

The compounds of this invention can exist as the individual stereoisomers as well as the racemic mixture. Accordingly, the compounds of the present invention will include not only the dl-racemates, but also their respective optically active d- and l-isomers.

As pointed out above, the invention includes the pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such oxalic acid and maleic acid.

The following compounds further illustrate compounds contemplated within the scope of the present invention:
  N-Methyl-3-[4-(trifluoromethoxy)phenoxy-3-phenyl-propanamine phosphate
  N,N-Dimethyl-3-[4-(trifluoromethoxy)phenoxy]-3-phenylpropanamine hydrochloride
  N,N-Dimethyl-3-[4-(methylthio)phenoxy-3-phenyl-propanamine formate
  N,N-Dimethyl-3-[4-(trifluoromethylthio)phenoxy]-3-phenylpropanamine
  4-[3-(Methylamino)-1-phenylpropoxy]benzenesulfonamide sulfate
  N-{4-[1-phenyl-3-(methylamino)propoxy]phenyl}methanesulfonamide oxalate
  4-[3-(Dimethylamino)-1-phenylpropoxy]benzamide maleate
  4-[3-(Methylamino)-1-phenylpropoxy]benzamide succinate
  N,N-Dimethyl-3-[4-(methylsulfinyl)phenoxy]-3-phenylpropanamine hydrobromide
  N-Methyl-3-[4-(methylsulfinyl)phenoxy]-3-phenyl-propanamine lactobionate N,N-Dimethyl-3-[4-(methylsulfonyl)phenoxy]-3-phenylpropanamine oxalate N-Methyl-3-[4-(methylsulfonyl)phenoxy]-3-phenylpropanamine N,N-Dimethyl-3-[4-(ethylthio)phenoxy]-3-phenylpropanamine hydrobromide N,N-Dimethyl-3-[4-(ethylsulfinyl)phenoxy]-3-phenylpropanamine N,N-Dimethyl-3-[4-(ethylsulfonyl)phenoxy]-3-phenylpropanamine citrate N-Methyl-3-[4-(ethylthio)phenoxy]-3-phenylpropanamine maleate N-Methyl-3-[4-(ethylsulfinyl)phenoxy]-3-phenylpropanamine naphthalene-1-sulfonate N-Methyl-3-[4-(ethylsulfonyl)phenoxy]-3-phenylpropanamine The compounds of the present invention may be prepared by procedures well known to those of ordinary skill in the art. The compounds are preferably synthesized by treating an hydroxy intermediate with an alkali metal hydride to form the corresponding alkali metal salt, which is then reacted with an appropriate compound containing a good leaving group to provide the corresponding 3-phenoxy-3-phenylpropanamine of the invention. This reaction may be represented by the following scheme:

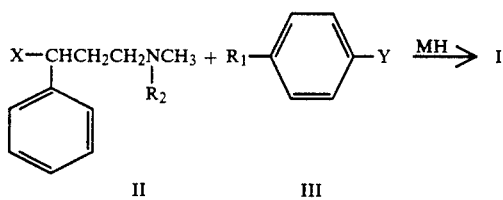

wherein M is an alkali metal, $R_1$ and $R_2$ are as defined above, and one of X and Y is hydroxy and the other is a good leaving group such as p-toluenesulfonyl, methanesulfonyl, triphenylphosphine oxide, halo and the like. Preferably X is hydroxy and Y is halo.

This reaction is carried out by combining approximately equimolar quantities to a slight excess of the alkali metal hydride with the alcohol to provide the corresponding alkali metal salt. Typical alkali metal hydrides include sodium hydride and potassium hydride. The compound is then reacted with an equimolar quantity to slight excess of the compound having the good leaving group. The reaction is conducted in a suitable aprotic solvent such as N,N-dimethylformamide, N,N-dimethylacetamide and related solvents. The reaction is substantially complete after about 10 minutes to about 24 hours when conducted at a temperature in the range of about 25° C. to about 150° C. More preferably, the reaction mixture will be complete within about 30 minutes to about 6 hours when conducted at a temperature in the range of about 75° C. to about 125° C. The product may be isolated by standard conditions as well. Typically, the mixture is diluted with water and extracted with a water immiscible organic solvent such as diethyl ether, ethyl acetate, chloroform and the like. The organic extracts are typically combined and dried. Following evaporation of the organic solvent the isolated residue may be further purified, if desired, by standard techniques such as crystallization from common solvents, or chromatography over solid supports such as silica gel or alumina.

The compounds of the present invention wherein $R_2$ is hydrogen are preferably prepared by demethylating the corresponding N,N-dimethylpropanamine. Preferably, a reagent such a phenyl chloroformate or trichloroethyl chloroformate is reacted with the N,N-dimethylpropanamine to provide the corresponding urethane intermediate, which is then hydrolyzed in base to provide the corresponding N-methylpropanamine.

A variation of the above scheme can also be used to prepare the sulfonamido compounds of this invention (I, $R_1=CH_3SO_2NH-$). The reaction is performed employing a 4-nitro- or 4-protected amino phenyl halide analogous to Formula III with the alcohol II (X=OH) to form the corresponding 4-nitro or 4-protected-amino analog of I. If the nitro intermediate is prepared, it may be chemically or catalytically reduced to the corresponding amine. Heating the nitro compound with stannous chloride in ethanol for 30–60 minutes is a preferred method of effecting this transformation. See Tetrahedron Letters, 25, 839 (1984). Alternatively, a protected amino group can be deblocked by conventional means to prepare the amino intermediate.

The amino intermediate can then be converted to the methanesulfonamido compound of this invention upon treatment with methanesulfonyl chloride, preferably in the presence of an acid scavenger, such as pyridine.

An alternate method of preparing the sulfoxide (p=1) and sulfone (p=2) compounds of this invention involves oxidizing the corresponding thio derivative (p=0) of Formula I. The thio derivatives may be transformed into the corresponding sulfoxide compounds upon treatment with a mild oxidizing agent, such as hydrogen peroxide in methanol, meta-chloroperbenzoic acid (MCPBA) in methylene chloride at 0° C., or an alkali metal periodate in aqueous alcohol. The corresponding sulfones are prepared from the thio or sulfoxide compounds on treatment with a strong oxidizing agent such as hydrogen peroxide in acetic acid or m-chloroperbenzoic acid in methylene chloride at 20°–30° C.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and the like.

The compounds employed as starting materials in the synthesis of the compounds of the invention are also prepared by standard procedures. Preferably, standard Mannich reaction conditions are employed to synthesize the corresponding Mannich Base from the appropriate ketone, formaldehyde and dimethylamine, which is then reduced with a hydride reducing agent, such as sodium borohydride, employing standard reduction conditions. The analogs containing the leaving group are also prepared by known procedures or are commercially available from various organic laboratories.

The pharmaceutically acceptable acid addition salts of the invention are typically formed by reacting a 3-phenyloxy-3-phenylpropanamine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

N,N-Dimethyl-γ-[4-(methylthio)phenoxy]benzenepropanamine ethanedioate

A. Preparation of 3-dimethylamino-1-phenyl-1-propanol

To a solution of 313.7 g of 3-dimethylaminopropiophenone hydrochloride in 750 ml of methanol and 375 ml of water was added a saturated solution of potassium carbonate until the pH of the solution was 10. The solution was cooled to 0° C. by means of an external ice bath at which time 27.8 g of sodium borohydride were added in portions over a 4-hour period. The ice bath was removed and the reaction mixture stirred at room temperature overnight. The methanol was removed in vacuo and the resulting solution diluted with water and extracted four times with diethyl ether. The combined ether extracts were washed once with water, once with a saturated sodium chloride solution, dried over sodium sulfate, and concentrated in vacuo to provide an oil. The oil was taken up in 300 ml of hexanes and chilled overnight. The resulting crystals were recovered by filtration providing 172 g of desired subtitle intermediate as a white crystalline solid, m.p.=45°–46° C.

Analysis calculated for $C_{11}H_{17}NO$: Theory: C, 73.70; H, 9.56; N, 7.81; Found: C, 73.74; H, 9.77; N, 7.73.

B. Preparation of 3-dimethylamino-1-phenyl-1-propyl chloride hydrochloride

To a solution of 75.06 g of the alcohol from Example 1A above in 500 ml of methylene chloride was bubbled hydrogen chloride gas for approximately 30 minutes with external ice cooling. Addition of the hydrogen chloride was ceased, the ice bath was removed, and 32.7 ml of thionyl chloride were added in dropwise fashion. After the addition was complete, the reaction mixture was heated at reflux for 2 hours and then stirred overnight at room temperature. The reaction mixture was treated with 500 ml of hexanes and cooled to 0° C. for 2 hours. The resulting precipitate was recovered by filtration and washed with hexanes providing 92.75 g of the desired subtitle intermediate, m.p. 159°–160° C.

Analysis calculated for $C_{11}H_{16}ClN.HCl$: Theory: C, 56.42; H, 7.32; N, 5.98; Found: C, 56.62; H, 7.17; N, 6.15.

C. Preparation of N,N-dimethyl-γ-[4-(methylthio)phenoxy]benzenepropanamine ethanedioate To a solution of 9.0 g of 4-methylthiophenol in 40 ml of dimethylformamide cooled by means of an external ice bath were added 2.56 g of a 60% sodium hydride dispersion in oil. After hydrogen evolution ceased, 5 g of the chloro intermediate from Example 1B above were added to the reaction mixture. After stirring overnight at room temperature, water was added to the reaction mixture, and 5N sodium hydroxide solution was added to adjust the pH to 14. The solution was extracted three times with diethyl ether. The combined ether extracts were washed twice with water, once with a saturated sodium chloride solution, dried over sodium sulfate, and concentrated in vacuo. The resulting product was purified by high pressure liquid chromatography over silica gel eluting with a 5% methanol/1% ammonium hydroxide/methylene chloride gradient. The appropriate fractions were combined and concentrated in vacuo to provide 4.55 g of a clear oil. The oxalate salt was prepared by treating 492 mg of the oil with one equivalent of oxalic acid and crystallized from ethyl acetate/methanol to provide 300 mg of the desired title product, m.p. 133°–135° C.

Analysis calculated for $C_{18}H_{23}NOS.C_2H_2O_4$: Theory: C, 61.36; H, 6.44; N, 3.58; Found: C, 61.12; H, 6.33; N, 3.46.

EXAMPLE 2

N-Methyl-γ-[4-(methylthio)phenoxy]benzenepropanamine ethanedioate

To a solution of 2.48 g of the N,N-dimethyl-γ-[4-(methylthio)phenoxy]benzenepropanamine base of Example 1C above in 100 ml of toluene were added 1.1 ml of phenyl chloroformate as the solution was heated at reflux. After the addition was complete, the solution was heated at reflux for 6 hours and stirred overnight at room temperature. The toluene was washed sequentially with 1N sodium hydroxide (twice), water, 1N hydrochloric acid (twice), water, and a saturated sodium chloride solution, dried over sodium sulfate, and concentrated in vacuo to provide 4.6 g of the phenyl urethane intermediate which was then dissolved in 100 ml of propylene glycol. Ten equivalents of 5N sodium hydroxide were added and the solution heated to 110° C. for 3 hours. After cooling to room temperature, the solution was diluted with water and extracted three times with diethyl ether. The combined ether extracts were washed twice with water, once with a saturated sodium chloride solution, dried over sodium sulfate, and concentrated in vacuo to provide 2.3 g of an oil. The oil was dissolved in ethyl acetate and added to a solution of oxalic acid in ethyl acetate. The resulting precipitate was recovered by filtration affording 1.22 g of a desired title product, m.p. 158°–159° C.

Analysis calculated for $C_{17}H_{21}NO.C_2H_2O_4$: Theory: C, 60.46; H, 6.14; N, 3.71; Found: C, 60.66; H, 6.25; N, 3.93.

EXAMPLE 3

N-Methyl-γ-{4-[(trifluoromethyl)thio]phenoxy}benzenepropanamine ethanedioate

To a suspension of 2 g of a 60% sodium hydride mineral oil dispersion and 25 ml of N,N-dimethylacetamide were added a solution of 8.26 g of α-[2-(methylamino)ethyl]benzenemethanol in 75 ml of N,N-dimethylacetamide over a 30-minute period. After stirring for one hour, the mixture was heated at 50°–60° C. for 30 minutes. p-Bromophenyl trifluoromethyl sulfide (12.85 g) was added and the mixture heated at 100° C. for 2.5 hours. After cooling, the mixture was stirred at room temperature overnight. The solution was poured into 250 ml of cold water and extracted three times with diethyl ether. The combined ether extracts were washed first with water, then with a saturated sodium chloride solution, dried over sodium sulfate, and evaporated in vacuo. The resulting oil was purified by high pressure liquid chromatography over silica gel eluting with methylene/chloride/methanol/ammonium hydroxide (100:5:1). The appropriate fractions were combined and evaporated to provide 1.59 g of the title product base as an oil. The oxalate salt was made in warm ethyl acetate and the resulting product crystallized from isopropanol to provide 1.64 g of the title product as colorless crystals, m.p. 173°–174° C. (with decomposition).

Analysis calculated for $C_{19}H_{20}F_3NO_5S$: Theory: C, 52.90; H, 4.67; N, 3.25; Found : C, 53.20; H, 4.80; N, 3.08.

EXAMPLE 4

4-[3-(Dimethylamino)-1-phenylpropoxy]benzenesulfonamide ethanedioate

To a mixture of 20.8 g of 4-hydroxybenzenesulfonamide in 160 ml of methanol were added 4.9 g of sodium hydroxide pellets. After dissolution had occurred, 9.4 g of 3-dimethylamino-1-phenyl-1-propyl chloride hydrochloride were added and the reaction mixture heated at reflux for 48 hours. After cooling, the methanol was removed by evaporation and excess 5N sodium hydroxide was added. The mixture was extracted three times with diethyl ether. The aqueous solution was acidified with concentrated hydrochloric acid and extracted three times with diethyl ether. The combined ether extracts were washed with water, a 10% sodium bicarbonate solution, and a saturated sodium chloride solution, dried over sodium sulfate, and evaporated in vacuo. The oxalate salt was prepared in warm ethyl acetate and recrystallized from methanol to provide 587 mg of the desired title product, m.p. 179°–181° C. (with decomposition).

Analysis calculated for $C_{19}H_{24}N_2O_7S$: Theory: C, 53.76; H, 5.70; N, 5.60; Found: C, 54.02; H, 5.97; N, 6.73.

EXAMPLE 5

N-{4-[1-Phenyl-3-(dimethylamino)propoxy]phenyl}methanesulfonamide

A. Preparation of N,N-dimethyl-γ-(4-nitrophenoxy)benzenepropanamine

Following the procedure of Example 3, 17.9 g of 3-dimethylamino-1-phenyl-1-propanol and 14.1 g of 1-fluoro-4-nitrobenzene were reacted to provide 26.54 g of the subtitle intermediate as a red oil. Preparation of the oxalate salt of a small portion of the oil provided yellow crystals with a melting point of 155°–157° C. (with decomposition).

B. Preparation of N,N-dimethyl-γ-(4-aminophenoxy)benzenepropanamine

Three grams of the nitro compound from Example 5A above were dissolved in 20 ml of 2B ethanol under a nitrogen atmosphere. With stirring, 11.3 g of stannous chloride dihydrate were added. After heating at 70° C. for 30 minutes, the solution was cooled and poured into 200 ml of ice. The mixture was made basic with 5N sodium hydroxide solution and extracted with diethyl ether. The organic extract was washed twice with a saturated sodium chloride solution, dried over sodium sulfate, and evaporated in vacuo to provide 1.86 g of an oil which crystallized on standing in the refrigerator. Recrystallization from hexanes provided 810 mg of the desired subtitle intermediate, m.p. 82°–84° C.

C. Preparation of N-{4-[1-phenyl-3-(dimethylamino)propoxy]phenyl}methanesulfonamide A solution of 5.25 g of N,N-dimethyl-γ-(4-aminophenoxy)benzenepropanamine in 30 ml of pyridine cooled to 10° C. by means of an external ice bath was treated with 1.86 ml of methanesulfonylchloride under a nitrogen atmosphere. The ice bath was removed and the reaction mixture stirred at room temperature overnight. The solution was poured into 30 ml of water, treated with acid and evaporated in vacuo. The residue was purified by high pressure liquid chromatography over silica gel eluting with methylene chloride/methanol/ammonium hydroxide (100:5:1). The appropriate fractions were combined and concentrated in vacuo providing 4.15 g of an oil which crystallized upon cooling. Recrystallization from ethanol provided 2.5 g of the desired title product as off-white crystals, m.p. 145°–147° C.

Analysis calculated for $C_{18}H_{24}N_2O_3S$: Theory: C, 62.04; H, 6.94; N, 8.04; Found: C, 61.94; H, 6.96; N, 7.91.

As noted above, the compounds of this invention are useful for inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

The term "pharmaceutically effective amount", as used herein, represents an amount of a compound of the invention which is capable of inhibiting serotonin uptake. The particular dose of compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. The compounds of the invention unexpectedly selectively inhibit the uptake of serotonin in mammals. It is a special feature of the compounds that they have good oral bioavailability without losing their substantial potent inhibiting effect of serotonin uptake. It is also a special feature of the compounds of the present invention in that they have been found to demonstrate a surprisingly low degree of toxicity in mammals. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by brain serotoninergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at rates set forth above for inhibiting serotonin uptake in mammals.

The following experiment was conducted to demonstrate the ability of the compounds of the present invention to inhibit the uptake of serotonin and norepinephrine. This general procedure is set forth by Wong et al., in *Drug Development Research* 6:397–403 (1985).

Male Sprague-Dawley rats (110–150 g) from Harlan Industries (Cumberland, Ind.) were fed a Purina Chow ad libitum for at least 3 days before being used in the studies. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin($^3$H-5-hydroxytryptamine, $^3$H-5HT) and $^{14}$C-1-norepinephrine ($^{14}$C-NE) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA, 50nM $^3$H-5HT and 100 nM $^{14}$C-NE. The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and were transferred to a counting vial containing 10 ml of scintillation fluid (PCS, Amersham, Arlington Heights, Ill.). Radioactivity was measured by a liquid scintillation spectrophotometer. Accumulation of $^3$H-5HT and $^{14}$C-NE at 4° C. represented the background and was subtracted from all samples.

The results of the evaluation of various compounds of the present invention are set forth below in Table I. In the Table, column 1 identifies the Example number of the compounds evaluated, and columns 2 and 3 provide the concentration of the test compound at $10^{-9}$ M (nM) needed to inhibit 50% of serotonin (5HT) or norepinephrine, respectively, and is indicated in the Table as IC$_{50}$. The numbers in parentheses represent percent inhibition at 1000 nM.

TABLE I

INHIBITION OF 5HT AND NOREPINEPHRINE UPTAKE IN VITRO

| Compound of Example No. | IC$_{50}$ (nM) 5HT | NE |
|---|---|---|
| 1 | 160 | >1000 (18) |
| 2 | 48 | 704 |
| 3 | >1000 (39) | >1000 (9) |
| 4 | >1000 (15) | >1000 (0) |
| 5 | >1000 (30) | >1000 (15) |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| N,N-Dimethyl-γ-[4-(methylthio)-phenoxy]benzenepropanamine ethanedioate | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| N-Methyl-γ-[4-(methylthio)phenoxy]-benzenepropanamine ethanedioate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|   | Weight % |
|---|---|
| N-Methyl-γ-{4-[(trifluoromethyl)thio]-phenoxy}benzenepropanamine ethanedioate | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

Formulation 4

Tablets each containing 60 mg of active ingredient are made as follows:

| 4-[3-(Dimethylamino)-1-phenylpropoxy]-benzenesulfonamide ethanedioate | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| N-{4-[1-Phenyl-3-(dimethylamino)propoxy]-phenyl}methanesulfonamide ethanedioate | 80 mg |
|---|---|
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| N-Methyl-γ-{4-[(trifluoromethyl)thio]-phenoxy}benzenepropanamine sulfate | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| N-Methyl-γ-[4-(methylthio)phenoxy]-benzenepropanamine hydrochloride | 50 mg |
|---|---|
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| 4-[3-(Dimethylamino)-1-phenylpropoxy]-benzenesulfonamide phosphate | 100 mg |
|---|---|
| isotonic saline | 1000 ml |

The solution of the above ingredients is administered intravenously at a rate of 1 ml per minute to a subject suffering from depression.

We claim:

1. A compound of the formula

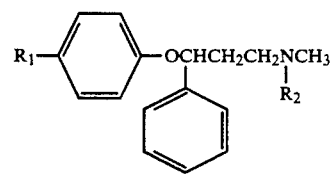

(I)

wherein:
R$_1$ is C$_1$ alkyl-S—, CF$_3$S—, CF$_3$O—, H$_2$NCO—, H$_2$NSO$_2$—, or CH$_3$SO$_2$NH—;
R$_2$ is hydrogen or methyl; or
the pharmaceutically acceptable acid addition salts thereof,
provided that when the compound is a pharmaceutically acceptable acid addition salt of C$_1$alkyl-S—; the salt must be hydrochloride, oxalate, maleate, or fumarate.

2. A compound of claim 1 wherein R$_2$ is hydrogen.

3. A compound of claim 1 wherein R$_2$ is methyl.

4. A compound of claim 2 which is N-methyl-γ-[4-(methylthio)phenoxy]benzenepropanamine hydrochloride.

5. A compound of claim 3 which is N,N-dimethyl-γ-[4-(methylthio)phenoxy]benzenepropanamine hydrochloride.

6. A method for inhibiting serotonin uptake in mammals which comprises administering to a mammal requiring increased neurotransmission of serotonin an effective amount of a compound of claim 1.

7. A method of claim 6 employing a compound wherein $R_2$ is hydrogen.

8. A method of claim 7 wherein the compound is N-methyl-γ-[4-(methylthio)phenoxy]benzenepropanamine hydrochloride.

9. A method of treating depression in humans comprising administering to a human suffering from depression an effective antidepressant dose of a compound of claim 1.

10. A method claim 9 employing a compound wherein $R_2$ is hydrogen.

11. A method of claim 10 wherein the compound is N-methyl-γ-[4-(methylthio)phenoxy]benzenepropanamine hydrochloride.

12. A method of treating obesity in humans comprising administering to a human suffering from obesity an effective antiobesity dose of a compound of claim 1.

13. A method of claim 12 employing a compound wherein $R_2$ is hydrogen.

14. A method of claim 13 wherein the compound is N-methyl-γ-[4-(methylthio)phenoxy]benzenepropanamine hydrochloride.

15. A method of suppressing the desire of humans to smoke comprising administering to a human in need of such suppression an effective dose to relieve the desire to smoke of a compound of claim 1.

16. A method of claim 15 employing a compound wherein $R_2$ is hydrogen.

17. A method of claim 16 wherein the compound is N-methyl-γ-[4-(methylthio)phenoxy]benzenepropanamine hydrochloride.

18. A method of suppressing the desire of humans to consume alcohol comprising administering to a human in need of such suppression an effective dose to relieve the desire to consume alcohol of a compound of claim 1.

19. A method of claim 18 employing a compound wherein $R_2$ is hydrogen.

20. A method of claim 19 wherein the compound is N-methyl-γ-[4-(methylthio)phenoxy]benzenepropanamine hydrochloride.

21. A pharmaceutical formulation comprising a compound of claim 1 and a pharmaceutically acceptable carrier, a diluent or excipient therefor.

22. A formulation of claim 21 employing a compound wherein $R_2$ is hydrogen.

23. A formulation of claim 22 wherein the compound is N-methyl-γ-[4-(methylthio)phenoxy]benzenepropanamine hydrochloride.

* * * * *